United States Patent [19]

Möhring et al.

[11] 4,152,350

[45] May 1, 1979

[54] PROCESS FOR THE PREPARATION OF POLYISOCYANATES CONTAINING BIURET GROUPS

[75] Inventors: Edgar Möhring, Bergisch-Gladbach; Küno Wagner; Hanns P. Müller, both of Leverkusen, all of Fed. Rep. of Germany

[73] Assignee: Bayer Aktiengesellschaft, Leverkusen, Fed. Rep. of Germany

[21] Appl. No.: 850,888

[22] Filed: Nov. 14, 1977

[30] Foreign Application Priority Data

Dec. 3, 1976 [DE] Fed. Rep. of Germany ....... 2654745

[51] Int. Cl.$^2$ ............................................. C07C 127/24
[52] U.S. Cl. .............................. 260/453 AB; 521/160; 528/59; 560/24; 560/32; 560/115; 560/159
[58] Field of Search .................. 260/453 AB; 560/159

[56] References Cited

U.S. PATENT DOCUMENTS

| 3,358,010 | 12/1967 | Britain | 260/453 AB |
| 3,862,973 | 1/1975 | Dietrich et al. | 260/453 AB |
| 3,903,126 | 9/1975 | Woerner et al. | 260/453 AB |
| 3,903,127 | 9/1975 | Wagner et al. | 260/453 AB |

*Primary Examiner*—Dolph H. Torrence
*Attorney, Agent, or Firm*—Gene Harsh; Lawrence S. Pope; Frederick H. Colen

[57] ABSTRACT

This invention relates to an improved process for the preparation of polyisocyanate mixtures containing biuret groups by the reaction of organic diisocyanates with compounds which react with isocyanate groups to form biuret groups, to the polyisocyanate mixtures obtained by this process and to the use thereof for the preparation of polyurethane resins by the isocyanate polyaddition process.

10 Claims, No Drawings

PROCESS FOR THE PREPARATION OF POLYISOCYANATES CONTAINING BIURET GROUPS

BACKGROUND OF THE INVENTION

It is known, for example, to prepare polyisocyanates containing biuret groups from diisocyanates and water (German Patent No. 1,101,394 and U.S. Pat. No. 3,124,605), hydrogen sulphide (German Patent No. 1,165,580 and Canadian Patent No. 757,637), formic acid (German Patent No. 1,174,760 and U.S. Pat. No. 3,350,438) or tertiary alcohols (German Patent No. 1,543,178 and U.S. Pat. No. 3,358,010). In these reactions, amino groups are first formed from the isocyanate groups in the diisocyanate starting material and these amino groups react with excess diisocyanate to form the biuret polyisocyanates by way of the corresponding urea diisocyanates.

These known processes have numerous disadvantages. In the heterogeneous reaction of diisocyanates with water, there is a risk of formation of insoluble polyureas which are difficult to separate. Furthermore, the above-mentioned known processes invariably give rise to gaseous by-products, such as carbon dioxide, carbon monoxide, carbon sulphoxide or olefins. Lastly, it is particularly disadvantageous that, in these known processes, some of the isocyanate groups of the diisocyanate used as starting material must be destroyed by amine formation. There has, therefore, been no lack of attempts to prepare polyisocyanates containing biuret groups by direct reaction of polyamines with polyisocyanates without any volatile by-products being split off and without destruction of the isocyanate groups by amine formation. However, owing to the high reactivity of the amino groups with the isocyanate groups, these attempts met with considerable practical difficulties due to the formation of large quantities of insoluble polyureas and cross-linked products. The only processes which met with some success were, therefore, those in which very particular starting materials were used. According to German Auslegeschrift No. 1,215,365 and U.S. Pat. No. 3,441,588, for example, higher molecular weight diamino polyethers must be used as diamine component to prevent the formation of the above-mentioned sparingly soluble by-products. It goes without saying that the necessity first to prepare diamino polyethers by a difficult process cannot be a technically completely satisfactory solution to the problem. The process according to German Offenlegungsschrift No. 1,963,190 and U.S. Pat. No. 3,824,266 is restricted to the use of diprimary aromatic diamines which have reduced reactivity due to steric or electronic effects.

The process according to German Offenlegungsschrift No. 2,261,065 and U.S. Pat. No. 3,903,126 also does not provide a technically feasible method of preparing polyisocyanates containing biuret groups by direct reaction of organic polyisocyanates with simple aliphatic and/or cycloaliphatic polyamines. According to Example 16 of these publications, the preparation of polyisocyanates containing biuret groups from hexamethylene diisocyanate and hexamethylene diamine requires reheating of the reaction mixture at 180° C. for 12 hours to complete the reaction. This long reheating at a high temperature is not only uneconomical but also leads to discoloration of the reaction product, particularly under large scale industrial production conditions, so that the use of these products in light-fast lacquers is strictly limited.

The indication given in general terms in U.S. Pat. No. 3,903,126 that the diamines may be used as mixtures with alcohols, in particular with diols, also does not give any concrete information as to how the difficulties described above could be overcome. In particular, the addition of small quantities of dipropylene glycol as described in Example 19 of the U.S. Pat. No. 3,903,126 affords no advantages over the use of a pure diamine (see Example 2 of the present application).

Although polyisocyanates having a biuret structure, in particular those based on hexamethylene diisocyanate, have attained a position of worldwide technical importance for the manufacture of light-fast and extremely weather-resistant lacquers having maximum gloss retention, polyisocyanates of this type are produced industrially and marketed with a small proportion of monomeric diisocyanate. Extensive toxicological investigations and many years experience in the processing of these products have shown that the upper limit of monomer content (hexamethylene diisocyanate) which may be tolerated in these polyisocyanates is about 0.7%, based on the solids content, because only then may safe working conditions with lacquers produced from them be ensured, provided that, in addition, the usual protective measures for working with lacquers are observed. The above-mentioned limit of about 0.7% has been accepted in the literature, for example, in the memorandum "PUR-Anstrichstoffe" of the deutsche gewerbliche Berufsgenossenschaft and in "Polyurethane Report" of the Paintmakers Association.

Recent extensive investigations have shown that when the above-mentioned polymolecular polyisocyanate mixtures having a biuret structure are stored for prolonged periods, particularly under uncontrolled conditions, for example, during transport in ships in hot climates, this limit of about 0.7% of monomeric hexamethylene diisocyanate is exceeded due to the catalytic action of the walls of the glass or metal containers and due to other as yet unknown catalytic effects and the presence of impurities which cannot be exactly analyzed, so that the monomer content may easily rise above about 1%.

Since it is possible to observe the limit of monomer concentration of about 0.7% under industrial conditions of producing the above-mentioned polyisocyanates and it has been proved for over a decade that such products may be safely processed, it is of the greatest importance for industrial and ecological reasons to increase the stability and reduce the breakdown into monomers and at the same time reduce the viscosity of the known biuret polyisocyanates, which are based on aliphatic or cycloaliphatic diisocyanates and which often have a viscosity of from about 10,000 to 120,000 cP at 20° C. Such reduction in the viscosity makes it possible to prepare one-component and two-component polyurethane lacquers without the use of solvents. Although a process for the preparation of exceptionally low viscosity polyisocyanates having a biuret structure, for example, on the basis of hexamethylene diisocyanate, has been described in U.S. Pat. No. 3,903,127, the polyisocyanates obtainable by this process also have the disadvantage of releasing monomeric hexamethylene diisocyanate in the course of prolonged storage.

It was, therefore, an object of the present invention to provide a process for the preparation of polyisocyanate mixtures containing biuret groups in which the disadvantages of the known processes would be substantially eliminated.

It has surprisingly been found that this problem may be solved in certain mixtures of alcohols, primary amines and, optionally, water, which will be described in more detail below, are used as "biuretizing agents".

By "biuretizing agents" are meant substances which react with organic isocyanates to form biuret groups.

SUMMARY OF THE INVENTION

The present invention relates to a process for the preparation of polyisocyanate mixtures containing biuret groups by the reaction of excess quantities of organic polyisocyanates with compounds which react with isocyanates to form biuret groups, characterized in that the organic polyisocyanates are reacted with a mixture containing:

(A) at least one monohydric primary, secondary or tertiary aliphatic or cycloaliphatic alcohol;

(B) at least one mono- or poly-amine having at least one aliphatically, cycloaliphatically or araliphatically bound primary amino group; and, optionally, (C) water or a compound from which water is split off.

DETAILED DESCRIPTION OF THE INVENTION

The following advantages are achieved by the process according to the present invention:

(1) Since water is not the exclusive biuretizing agent, both the proportion of isocyanate groups which must first be "destroyed" by amine formation and the quantity of gaseous by-products split off (carbon dioxide) are less than in the process according to German Patent No. 1,101,394 and U.S. Pat. No. 3,124,605 in which water alone is used as biuretizing agent;

(2) The resulting polyisocyanate mixtures having a biuret structure are distinguished by containing an exceptionally high proportion of biuret polyisocyanates corresponding to the following general formulae (I), (II) and allophanate polyisocyanates corresponding to the following general formula (III), and they, therefore, have an exceptionally low viscosity of preferably 1000 to 10000 cP/25° C.

(3) The viscosity is lowered by the allophanate polyisocyanates corresponding to the general formula (III) which are produced by the reaction of the polyisocyanates with the alcohol component and which function as reactive diluents;

(4) Light-colored reaction products free from gel particles are obtained which are particularly distinguished from the products obtained by the process of German Offenlegungsschrift No. 2,261,065 and U.S. Pat. No. 3,903,126 in that they may be freed from excess monomeric diisocyanate without the least difficulty, for example, by thin layer distillation;

(5) The products of the process produced using a monohydric primary aliphatic or cycloaliphatic alcohol as the alcohol component of the biuretizing agent mixture are particularly distinguished by the improved storage stability thereof, i.e., the reduced tendency to split off monomeric starting diisocyanate.

The biuretizing agent used in the process according to the present invention, that is to say the substances which react with isocyanates to form biuret structures, are mixtures of amines, alcohols and, optionally, water.

The proportions of amine component, alcohol component and water may vary within wide, uncritical ranges in the biuretizing agents used according to the present invention. The equivalent ratio of hydroxyl groups in component (A) to water (component (C)) is preferably from about 1:0 to 1:2 in the biuretizing agents used according to the present invention, while the equivalent ratio of (hydroxyl groups of component (A)+$H_2O$): (primary amino groups of component (B)) is preferably from about 5:1 to 1:5, most preferably from about 2:1 to 1:2.

The fact that mixtures of amines and alcohols and, optionally, water are quite different in their reactivity with isocyanate groups than the pure amines or alcohols or water alone is extremely surprising. In fact, one would have expected that the high reactivity of amines towards isocyanate groups, which is the main cause of the difficulties hitherto encountered in the preparation of biuret polyisocyanates by the reaction of diisocyanates with free amines, would not be reduced by the presence of alcohols and, optionally, water. On the other hand, one would have expected the less reactive alcohols and water, which is known to be considerably less reactive, to react more slowly with the isocyanates than the amines present in the mixture. In fact, the biuretizing agents according to the present invention behave as uniform compounds in the reaction thereof with isocyanate groups; i.e., they react much more slowly with isocyanates than do the corresponding amines, but more rapidly than the alcohols used and considerably more rapidly than water alone. The finding that the products according to the present invention which contain allophanate groups are more stable than the biuret polyisocyanate mixtures known in the art is also surprising since, so far as has hitherto been known, allophanate groups are less stable than biuret groups.

In the process according to the present invention, the biuretizing agents according to the present invention are reacted with an excess of polyisocyanate. The amount of polyisocyanate excess used may in principle be as high as desired, but in practice the reactants are generally used in such proportions that the equivalent ratio of isocyanate groups in the starting polyisocyanate to (primary amino groups+alcoholic hydroxyl groups+water) in the reaction mixture is from about 3:1 to 100:1, preferably from about 5:1 to 15:1. The reaction is generally carried out at temperatures of from about 60° to 200° C., preferably from about 120° to 180° C. Any cloudiness occurring in the course of the reaction may be eliminated by briefly heating the mixture to temperatures of from about 160° to 200° C. The biuretizing agent is generally added to the polyisocyanate with stirring. When all the biuretizing agent has been added, the temperature of the reaction mixture is generally maintained at from about 130° to 160° C. for from about 1 to 6 hours. The excess of monomeric diisocyanate or polyisocyanate may then be removed, for example, by thin layer evaporation. According to another particular embodiment of the process, the amine-alcohol-optional water mixture used as biuretizing agent is evaporated at elevated temperature and passed into the polyisocyanate which has been heated to from about 100° to 250° C., optionally together with a stream of inert gas (e.g., nitrogen). Extremely fine distribution of the mixture in the polyisocyanate is thereby achieved.

Organic amines or amine mixtures containing 1 or 2 aliphatically or cycloaliphatically bound primary amino groups are used for the process according to the present invention. Such amines include, for example, aliphatic or cycloaliphatic monoamines corresponding to the following general formula: R—NH₂ wherein R represents an aliphatic hydrocarbon group having from 1 to 12 carbon atoms or a cycloaliphatic hydrocarbon group having from 5 to 7 carbon atoms, such as methylamine, n-butylamine, n-dodecylamine, cyclopentylamine, cyclohexylamine or cycloheptylamine. It is preferred, however, to use polyamines containing two aliphatically or cycloaliphatically bound primary amino groups for the process according to the present invention. Examples of such amines include: diprimary diamines corresponding to the following general formula: R'(NH₂)₂ wherein R' represents an aliphatic hydrocarbon group having from 2 to 12 carbon atoms, a cycloaliphatic hydrocarbon group having from 4 to 17 carbon atoms or an araliphatic hydrocarbon group having from 8 to 10 carbon atoms, e.g., ethylene diamine; 1,2- and 1,3-propylene diamine; 1,4-diaminobutane; 2,2-dimethyl-propane diamine-(1,3); 1,6-diaminohexane; 2,5-dimethylhexane diamine-(2,5); 2,2,4-trimethylhexane diamine-(1,6); 1,8-diaminooctane; 1,10-diaminodecane; 1,11-undecane diamine; 1,12-dodecane diamine; 1-methyl-4-(amino isopropyl)cyclohexylamine-1; 3-aminomethyl-3,5,5-trimethyl-cyclohexylamine-(1); 1,2-bis-(aminomethyl)-cyclobutane; p-xylylene diamine; 1,4-bis-(2-aminoethyl)-benzene; 1,2- and 1,4-diaminocyclohexane; 1,2-; 1,4-; 1,5- and 1,8-diaminodecalin; 1-methyl-4-aminoisopropyl-cyclohexylamine-1; 4,4'-diamino-dicyclohexyl; 4,4'-diamino-dicyclohexyl methane; 2,2'-(bis-4-amino-cyclohexyl)-propane; 3,3'-dimethyl-4,4'-diamino-dicyclohexyl methane; 1,2-bis-(4-aminocyclohexyl)-ethane and 3,3',5,5'-tetramethyl-bis-(4-aminocyclohexyl)-methane and -propane. Mixtures of these exemplified amines may also be used.

Other suitable polyamines for the process according to the present invention include bis-(aminoalkyl)-amines, preferably those having a total of from 4 to 12 carbon atoms, e.g., bis-(2-aminoethyl)-amine, bis-(3-aminopropyl)-amine, bis-(4-aminobutyl)-amine and bis-(6-aminohexyl)-amine, and isomeric mixtures of dipropylene triamine and dibutylene triamine.

Tetramethylene diamine, 1,2-bis-(aminomethyl)-cyclobutane and especially hexamethylene diamine are preferably used.

Particularly suitable alcohols for the process according to the present invention include alcohols corresponding to the following general formula: Y-OH wherein Y represents a straight- or branched-chain aliphatic hydrocarbon group having from 1 to 15 carbon atoms or a cycloaliphatic hydrocarbon group having from 4 to 15 carbon atoms. Examples of such alcohols include: methanol, ethanol, 1-propanol, 2-propanol, 1-butanol, 2-butanol, 2-methyl-1-propanol, 2-methyl-2-propanol, 1-pentanol, 2-methyl-4-butanol, 2,2-dimethylpropanol, 1-hexanol, 2-methyl-4-pentanol, 2-ethyl-1-butanol, 1-octanol, 2-ethyl-1-hexanol, tertiary butanol, cyclohexanol, 2-, 3- and 4-methylcyclohexanol, hydroxymethyl cyclohexane; 3,3,5-trimethyl-cyclohexanol and 4-tertiary butyl-cyclohexanol.

The preferred alcohols are monohydric primary alcohols having from 1 to 4 carbon atoms, such as ethanol, propanol, n-butanol and i-butanol. Methanol is particularly preferred.

The water used as optional component (C) is present in the biuretizing agents used according to the present invention either as such or in the form of compounds which split off water, e.g., compounds containing water of crystallization (sodium sulphate, oxalic acid, chloralhydrate, formaldehyde hydrate) or dicarboxylic acids which readily change into anhydrides, such as maleic acid or salicylic acid, or N-methylol compounds.

Particularly suitable polyisocyanates for the process according to the present invention are diisocyanates corresponding to the following general formula: Q(NCO)₂ wherein Q represents an aromatic hydrocarbon group having from 6 to 15 carbon atoms, an araliphatic hydrocarbon group having from 8 to 12 carbon atoms, preferably having 8 carbon atoms, an aliphatic hydrocarbon group having from 4 to 12 carbon atoms or a cycloaliphatic hydrocarbon group having from 4 to 15 carbon atoms. Examples include: tolylene-2,4- and 2,6-diisocyanate and isomeric mixtures thereof, 4,4'- and 2,4'-diphenyl methane diisocyanate and xylylene diisocyanate. Aliphatic and cycloaliphatic diisocyanates, such as 1,4-diisocyanato butane, 1,6-diisocyanato hexane, 2,4,4-trimethyl hexane-1,6-diisocyanate, 1,11-diisocyanate undecane, 3-isocyanatomethyl-3,5,5-trimethylcyclohexyl isocyanate-1; 4,4'-cyclohexane diisocyanate, 4,4'-dicyclohexylmethanediisocyanate and 1,2-bis-(isocyanatomethyl)-cyclobutane, are particularly suitable. Hexamethylene diisocyanate is especially preferred.

Exceptionally light-colored products are obtained from the process according to the present invention if the diisocyanate used as starting material is preheated for several hours (from about 6 to 10 hours) at from about 120° to 195° C., preferably from about 160° to 180° C., and is then distilled.

The products obtained by the process according to the present invention are generally clear, colorless to yellowish, low viscosity to medium viscosity mixtures containing biuret polyisocyanates which, if they have been prepared from the preferred diamines together with monohydric, primary or secondary alcohols and water, consist predominantly of compounds corresponding to the general formulae (I), (II) and (III), regardless of the amount of diisocyanate excess employed.

In these formulae, Q, R' and Y have the meanings noted above.

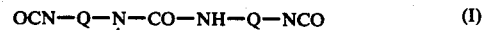
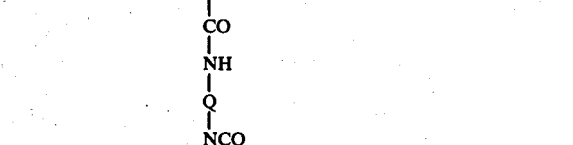
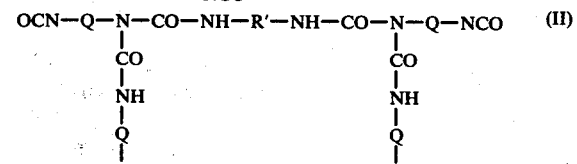

When starting materials of analogous constitution are reacted in the process according to the present invention, for example, when hexamethylene diamine/alcohol/water is reacted with hexamethylene diisocyanate ($Q=R'=(CH_2)_6$), transbiuretization reactions take place which give rise to biuret polyisocyanate mixtures containing an exceptionally high proportion of monobiurets corresponding to general formula (I), this formation again being substantially independent of the diisocyanate excess employed.

The process according to the present invention, therefore, provides a very elegant method of producing exceptionally low viscosity biuret polyisocyanate mixtures containing an exceptionally high proportion of monobiurets, simply by using diisocyanates and diamines which have an analogous constitution ($Q=R'$).

The products of the process according to the present invention are distinguished by exceptional solubility in the conventional lacquer solvents, such as acetone, dioxane, tetrahydrofuran, benzene, xylene, ethyl acetate and ethyl glycolacetate.

The products of the process may be used, for example, as crude solutions in the excess diisocyanates used for the preparation thereof or they may be used in isolated form or in mixtures with other polyisocyanates for producing and modifying synthetic resins, foam plastics of all types and lacquer coats.

One particular advantage of this is that a high proportion of the products of the process have such a low viscosity due to the reactive diluents corresponding to the general formula (III) that solvents may be completely dispensed with. This is a particularly important advantage for processing and for reducing environmental pollution.

Another particular advantage is that the products of the process produced using a monohydric primary aliphatic or cycloaliphatic alcohol as the alcohol component of the biuretizing agent mixture are to a very large extent stable against breakdown into the starting monomers.

After preparation and purification from monomeric diisocyanates and polyisocyanates, it is particularly advantageous to use the products as physiologically harmless polyisocyanates for the production of lacquer coats, either alone or in combination with the conventional polyisocyanates, to modify the properties of lacquer coatings. The products according to the present invention are particularly suitable for use as isocyanate components in two-component polyurethane lacquers. Particularly important for this purpose is the excellent compatibility thereof with the polyhydroxyl compounds normally used for this purpose, such as polyhydroxy polyacrylates, polyhydroxy polyethers or polyhydroxy polyesters. The reaction products which are free from monomers are also eminently suitable for the production of one-component lacquers since they react with atmospheric moisture in the presence of suitable catalysts, rapidly form dust-dry surfaces and are crosslinked and become insoluble within a short time.

The products of the process may also be used for the production of light-fast foams and porous synthetic resins having a high density and smooth surface skin.

The products may also be grafted in the presence of radical formers, for example, with acrylic acid derivatives or other suitable compounds, to give rise to modified polyisocyanates which have valuable properties.

The parts referred to in the Examples are parts, by weight.

EXAMPLES

EXAMPLE 1

19.2 parts (0.6 mol) of methanol are added to 18.0 parts (0.3 mol) of ethylene diamine and the mixture is homogenized. It is then introduced dropwise into 1211 parts (7.2 mol) of hexamethylene diisocyanate at 160° C. The reaction mixture is stirred for 10 hours at 175° C. Any particles floating in the solution are separated off. The clear reaction solution is freed from excess hexamethylene diisocyanate by thin layer evaporation at 168° C./0.5 Torr. 481 parts of a clear, yellowish polyisocyanate containing biuret groups and having an isocyanate content of 21.8%, by weight, a viscosity of 3283 cP/25° C. and a residual hexamethylene diisocyanate content of 0.10% are obtained.

Gel chromatographic analysis indicates the following composition:
22.1% allophanate (III)
25.6% monobiuret (I)
11.9% bis-biuret allophanate
8.9% bis-biuret (II)
5.6% tris-biuret allophanate
4.0% tris-biuret
21.8% unidentified or higher molecular weight constituents.

To determine the storage stability of this polyisocyanate mixture with regard to the tendency to break down into hexamethylene diisocyanate, 8 samples of the mixture were stored for 2, 4, 8 and 16 weeks at 25° C. and 50° C., and the free hexamethylene diisocyanate content was then determined by means of gas chromatography. The results obtained are summarized in the following Table.

Table

| Storage Time | Storage Temperature | Hexamethylene Diisocyanate Content |
| --- | --- | --- |
| 2 Weeks | 25° C. | 0.18 |
| 4 Weeks | 25° C. | 0.20 |
| 8 Weeks | 25° C. | 0.22 |
| 16 Weeks | 25° C. | 0.18 |
| 2 Weeks | 50° C. | 0.21 |
| 4 Weeks | 50° C. | 0.24 |
| 8 Weeks | 50° C. | 0.29 |
| 16 Weeks | 50° C. | 0.32 |

EXAMPLE 2 (Comparison Example)

This Example shows that a method analogous to that described in Example 1 using a small quantity of dipropylene glycol as described in Example 19 of U.S. Pat. No. 3,903,126 is hardly a technically feasible process for the preparation of polyisocyanates containing biuret groups and that considerable difficulties are encountered, particularly due to the formation of large quantities of insoluble polyureas which cannot be completely redissolved even by prolonged stirring. Thin layer evaporation and filtration are also impossible. The reaction on the whole proceeds as if a pure amine had been used.

10.5 parts (0.075 mol) of dipropylene glycol are added to 18.0 parts (0.3 mol) of ethylene diamine and the mixture is homogenized. This mixture is introduced dropwise into 1211 parts (7.2 mol) of hexamethylene diisocyanate at 160° C. Vigorous evolution of heat occurs and large quantities of polyurea are formed, accompanied by violent crackling and spitting at the point where the hexamethylene diisocyanate is introduced. The mixture is stirred for 10 hours at 175° C., during which time the product become reddish-brown in color.

Since undissolved polyurea is still present and filtration is impossible due to the presence of clear gel particles, no further attempts are made to work-up the product.

When this comparison experiment is repeated, but with the gradual dropwise addition of the mixture of ethylene diamine and dipropylene glycol to hexamethylene diisocyanate which is maintained at 25° C., no useful result is obtained since insoluble urea isocyanates immediately precipitate. When this suspension of urea diisocyanate in excess hexamethylene diisocyanate is heated to 165° C. with stirring, only small portions of the precipitate go into solution. At the same time, the solution turns reddish-brown. The unsuccessful experiment was stopped after 4 hours.

EXAMPLE 3

51.0 parts (0.3 mol) of 1-amino-3,3,5-trimethyl-5-aminomethyl cyclohexane are mixed with 19.2 parts (0.6 mol) of methanol and the mixture is introduced dropwise into 1211 parts (7.2 mol) of hexamethylene diisocyanate at 166° C. The mixture is then stirred for a further 20 minutes at 170° C. The product is worked-up indicated in Example 1. 336 parts of a clear yellow polyisocyanate which contains biuret groups and has an isocyanate content of 21.1%, a viscosity of 3815 cP/25° C. and a residual hexamethylene diisocyanate content of 0.52% are obtained. This residual hexamethylene diisocyanate content rises by only 0.08% during 4 weeks at 25° C.

Gel chromatographic examination shows the presence of a very high proportion of monobiuret (I):
  8.6% allophanate (III)
  43.8% monobiuret (I)
  15.6% bis-biuret (II)
  8.0% tris-biuret
  4.7% tetra-biuret
  18.8% unidentified or higher molecular weight constituents.

EXAMPLE 4

18.0 parts (0.3 mol) of ethylene diamine, 9.6 parts (0.3 mol) of methanol and 5.4 parts (0.3 mol) of water are mixed together and the mixture is introduced dropwise into 1211 parts (7.2 mol) of hexamethylene diisocyanate at 160° C. The mixture is then stirred for 5 hours at 180° C. Further working-up is as indicated in Example 1. 414 parts of a clear, golden-yellow polyisocyanate containing biuret groups and having an isocyanate content of 20.3%, a viscosity of 3924 cP/25° C. and a residual hexamethylene diisocyanate content of 0.38 are obtained.

Gel chromatographic investigation shows a distribution of components similar to that of Example 1:
  17.3% allophanate (III)
  28.8% mono-biuret (I)
  10.5% bis-biuret allophanate
  9.7% bis-biuret (II)
  5.2% tris-biuret allophanate
  4.6% tris-biuret
  23.5% unidentified or higher molecular weight constituents.

EXAMPLE 5

51.0 parts (0.3 mol) of 1-amino-3,3,5-trimethyl-5-aminomethyl cyclohexane, 9.6 parts (0.3 mol) of methanol and 5.4 parts (0.3 mol) of water are mixed together and the mixture is introduced dropwise into 1211 parts (7.2 mol) of hexamethylene diisocyanate at 166° C. The mixture is then stirred for 1 hour at 160° C. Further working-up is as indicated in Example 1. 399 parts of a clear, yellowish polyisocyanate which contains biuret groups and has an isocyanate content of 20.3%, a viscosity of 6944 cP/25° C. and a residual monomeric isocyanate content of 0.25% which only rises to 0.46% after 18 weeks at 50° C. are obtained.

Gel chromatographic analysis shows a similar distribution of components to that of Example 2:
  5.7% allophanate (III)
  41.0% mono-biuret (I)
  16.7% bis-biuret (II)
  9.2% tris-biuret
  6.9% tetra-biuret
  20.2% unidentified or higher molecular weight constituents.

EXAMPLE 6

51.0 parts (0.3 mol) of 1-amino-3,3,5-trimethyl-5-aminomethyl cyclohexane and 44.4 parts of tertiary butanol are mixed together and introduced dropwise into 1211 parts (7.2 mol) of hexamethylene diisocyanate at 168° C. The mixture is then stirred for 5 hours at 150° C. Further working-up is as described in Example 1. 489 parts of a clear, colorless polyisocyanate which contains biuret groups and has an isocyanate content of 21.6%, a viscosity of 8829 cP/25° C. and a residual monomeric isocyanate content of 0.6% are obtained.

Gel chromatographic investigation again shows the presence of a high proportion of monobiuret, as in Examples 2 and 4:
  1.4% urea
  37.3% mono-biuret (I)
  17.1% bis-biuret (II)
  10.3% tris-biuret
  7.4% tetra-biuret
  26.5% unidentified or higher molecular weight constituents.

EXAMPLE 7

18.0 parts (0.3 mol) of ethylene diamine and 22.3 parts (0.3 mol) of tertiary butanol are mixed together and introduced dropwise into 1211 parts (7.2 mol) of hexamethylene diisocyanate at 160° C. The mixture is then stirred for 4 hours at 190° C. Further working-up is as described in Example 1. 332 parts of a clear, yellow polyisocyanate containing biuret groups and having an isocyanate content of 21.2% and a viscosity of 3172 cP/25° C. are obtained.

EXAMPLE 8

34.8 parts (0.3 mol) of hexamethylene diamine and 44.5 parts (0.6 mol) of tertiary butanol are mixed together and introduced dropwise into 1211 parts (7.2 mol) of hexamethylene diisocyanate at 160° C. The mixture is then stirred for 2 hours at 180° C. Further working-up is as described in Example 1. 482 parts of a clear, yellow polyisocyanate which contains biuret groups and has an isocyanate content of 20.6%, a viscosity of 9701 cP/25° C. and a residual hexamethylene diisocyanate content of 0.55% are obtained.

EXAMPLE 9

34.8 parts (0.3 mol) of hexamethylene diamine and 19.2 parts (0.6 mol) of methanol are mixed together and then introduced dropwise at 160° C. into 1211 parts (7.2 mol) of hexamethylene diisocyanate. The mixture is then stirred for 3 hours at 190° C. Further working up is as described in Example 1. 278 parts of a clear, colorless polyisocyanate which contains biuret groups and has an isocyanate content of 21.3%, a viscosity of 1009 cP/25° C. and a residual hexamethylene diisocyanate content of 0.30% which rises to 0.52% after 16 weeks at 50° C. are obtained.

EXAMPLE 10

34.8 parts (0.3 mol) of hexamethylene diamine, 9.6 parts (0.3 mol) of methanol and 5.4 parts (0.3 mol) of water are mixed together and introduced dropwise at 160° C. into 1211 parts (7.2 mol) of hexamethylene diisocyanate. The resulting mixture is stirred for 3 hours at 190° C. and then for 1 hour at 150° C. Further working up is as described in Example 1. 321 parts of a clear, colorless polyisocyanate which contains biuret groups and has an isocyanate content of 21.6%, a viscosity of 2066 cP/25° C. and a residual hexamethylene diisocyanate content of 0.38% which rises by only 0.09% in the course of 4 weeks are obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of polyisocyanate mixtures containing biuret groups by the reaction of excess quantities of organic polyisocyanates with compounds which react with isocyanate groups to form biuret groups, characterized in that the organic polyisocyanates are reacted with a mixture with contains
    (A) at least one monohydric primary or secondary aliphatic or cycloaliphatic alcohol;
    (B) at least one monoamine or polyamine having at least one aliphatically, cycloaliphatically or araliphatically bound primary amino group; and, optionally,
    (C) water or a compound which splits off water.

2. A process according to claim 1, characterized in that the organic polyisocyanates are reacted with such quantities of the mixture of components (A), (B) and (C) that an equivalent ratio of isocyanate groups to (primary amino groups+alcoholic hydroxyl groups+water) of from about 3:1 to 100:1 is present.

3. A process according to claim 1, characterized in that components (A), (B) and (C) are put into the process in such quantities that the equivalent ratio of the hydroxyl groups of component (A) to water (component (C)) is from about 1:0 to 1:2 and the equivalent ratio of (hydroxyl groups of component (A)+water) to (primary amino groups of component (B)) is from about 2:1 to 1:2.

4. The process of claim 1 wherein the monohydric aliphatic or cycloaliphatic alcohol is a monohydric primary aliphatic or cycloaliphatic alcohol.

5. Polyisocyanate mixtures containing biuret groups obtainable according to the process of claim 4.

6. A process for the preparation of polyisocyanate mixtures containing biuret groups comprising reacting
    (A) excess quantities of organic polyisocyanates with
    (B) a biuretizing mixture comprising
        (i) at least one monohydric primary or secondary aliphatic or cycloaliphatic alcohol,
        (ii) at least one monoamine or polyamine having at least one aliphatically, cycloaliphatically or araliphatically bound primary amino group, and
        (iii) water or a compound which splits off water
    wherein the equivalent ratio of hydroxyl groups of component (i) to water is from about 1:0 to 1:2 and the equivalent ratio of hydroxyl groups of component (i) plus water to primary amino groups of component (ii) is from about 5:1 to 1:5.

7. The process of claim 6 wherein the equivalent ratio of isocyanate groups to hydroxyl groups of component (i) plus primary amino groups of component (ii) plus water is from about 3:1 to 100:1.

8. The process of claim 7 wherein the equivalent ratio of isocyanate groups to hydroxyl groups of component (i) plus primary amino groups of component (ii) plus water is from about 5:1 to 15:1.

9. The process of claim 6 wherein the equivalent ratio of hydroxyl groups of component (i) plus water to primary amino groups of component (ii) is from about 2:1 to 1:2.

10. The process of claim 6 wherein component (i) is a monohydric alcohol of the formula

wherein Y is a straight- or branched-chain aliphatic hydrocarbon group having from 1 to 15 carbon atoms or a cycloaliphatic hydrocarbon group having from 4 to 15 carbon atoms, and wherein component (ii) is a diamine of the formula

wherein R' is an aliphatic hydrocarbon group having from 2 to 12 carbon atoms, a cycloaliphatic hydrocarbon group having from 4 to 17 carbon atoms or an araliphatic group having from 8 to 10 carbon atoms.

* * * * *